United States Patent [19]

Tomcufcik et al.

[11] 3,931,152

[45] Jan. 6, 1976

[54] 2-(1,3-DIAZACYCLOALKENYL)-2-HYDRAZONES OF SUBSTITUTED CHALCONES

[75] Inventors: Andrew Stephen Tomcufcik, Old Tappan; Raymond George Wilkinson, Montvale, both of N.J.; Ralph Grassing Child, Pearl River, N.Y.

[73] Assignee: American Cyanamid Company, Stamford, Conn.

[22] Filed: Jan. 29, 1974

[21] Appl. No.: 437,549

[52] U.S. Cl. .................. 260/239 BC; 260/240 G; 260/256.4 H; 260/309.6; 424/244; 424/251; 424/273

[51] Int. Cl.² ........................................ C07D 243/04

[58] Field of Search .................. 260/239 BC, 240 G

[56] References Cited
UNITED STATES PATENTS

| | | | |
|---|---|---|---|
| 2,369,817 | 2/1945 | De Groote et al. | 260/239 BC |
| 3,468,887 | 9/1969 | Stahle et al. | 260/239 BC |

*Primary Examiner*—Donald G. Daus
*Assistant Examiner*—D. B. Springer
*Attorney, Agent, or Firm*—Denis A. Polyn

[57] ABSTRACT

The preparation of 2-(1,3-Diazacycloalkenyl)-2-hydrazones of substituted chalcones is described. These compounds are useful as anti-tubercular agents in warm-blooded animals.

13 Claims, No Drawings

2-(1,3-DIAZACYCLOALKENYL)-2-HYDRAZONES OF SUBSTITUTED CHALCONES

DESCRIPTION OF THE INVENTION

The compounds of this invention can be illustrated as those of the formula:

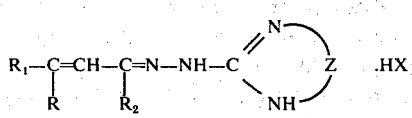

wherein $R_1$ and $R_2$ may be the same or different and are selected from the group consisting of monohalophenyl; dihalophenyl; monomethylphenyl; dimethylphenyl; trimethylphenyl; tetramethylphenyl; monoalkoxy $C_1$-$C_4$ phenyl; dialkoxy $C_2$-$C_8$ phenyl; $C_1$-$C_4$ alkylthiophenyl; methylsulfonylphenyl; trifluoromethylphenyl; anthryl; naphthyl and biphenylyl; R is hydrogen; methyl or chlorophenyl; Z is

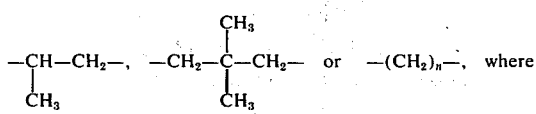

$n = 2$, 3 or 4; X is chloro; iodo or bromo.

The present compounds are usually crystalline solids and as salts are somewhat soluble in water.

One method of preparing compounds of the present invention is illustrated by the following reaction:

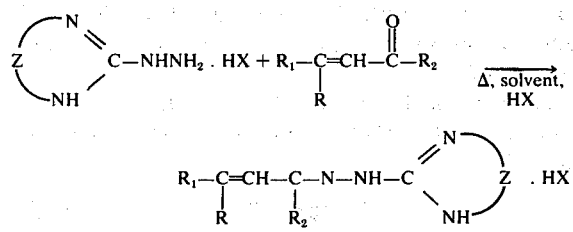

wherein R, $R_1$, $R_2$, Z and X are as defined hereinbefore.

The reaction is carried out in a hydrophilic solvent such as ethanol, n-propanol, butanol, dioxane, 2-methoxyethanol, etc., at a temperature which may vary from about 70°C. to 140°C. The time for completing the reaction may vary from about 0.5 to 16 hours. As catalyst a small portion of hydrohalic acid (HX) may be added to the reaction mixture.

The compounds of the present invention are active against *Mycobacterium tuberculosis* H37Rv infections in mice when tested in accordance with the following procedure: Carworth Farms CF1 white mice, females, 4 to 6 weeks old, weighing 17 to 22 grams, are infected with *Mycobacterium tuberculosis* H37Rv by administration intravenously of 0.2 ml. of a buffered saline suspension containing approximately 1.5 mg./ml. wet weight of a 12 to 14 day culture of the test organism grown on Sauton's agar medium. Routinely, 200–300 mice are given this standard infection and then segregated in a random manner into cages each of which holds 5 or 10 mice. Four groups of 5 mice each are retained as untreated controls and the remaining mice are used to ascertain activity of the compounds under test. During a 1 year experience with this test, the standard infection defined above caused a 99.5% mortality, in that 756 of the 760 infected untreated control mice diet within 28 days, the normal period of the test.

A measured amount of each compound to be tested is administered orally incorporated in a Standard Diet to groups of infected mice for 14 days, after which the mice are fed untreated Standard Diet. Control animals receive untreated Standard Diet for the entire test period and all animals are allowed to feed at will. Tests are terminated 28 days after the day of infection. A compound is judged active if it either saves 1 or 2 of 2 mice in a test group, or 2 or more of 5 mice in a test group in two tests, or prolongs average survival time by 4 or more days compared to untreated controls.

The Standard Diet used in this test procedure is a commercial feed designated for laboratory mice and rats composed of the following ingredients: Animal liver meal, fish meal, dried whey, corn and wheat flakes, ground yellow corn, ground oat groats, dehulled soybean meal, wheat germ meal, wheat middlings, cane molasses, dehydrated alfalfa meal, soybean oil, brewers' yeast, irradiated dried yeast (source of Vitamin $D_2$), riboflavin, niacin, calcium pantothenate, choline chloride, Vitamin A palmitate, D-activated animal sterol, $\alpha$-tocopherol, dicalcium phosphate, thiamine hydrochloride, menadione sodium bisulfite (source of Vitamin K activity), salt and traces of manganous oxide, copper sulfate, iron carbonate, potassium iodate, cobalt sulfate and zinc oxide. This commercial feed has the guaranteed analysis as containing a minimum of 24.0% crude protein, a minimum of 4.0% crude fat and a maximum of 4.5% crude fiber and is sold under the trademark Wayne Lab-Blox by Allied Mills, Inc., Chicago, Illinois.

In the test procedure described hereinabove, the Standard Diet, into which measured amounts of the test compounds had been homogeneously incorporated was administered to infected test animals, whereas untreated Standard Diet was given to infected control animals.

The following Table I shows the activity against *Mycobacterium Tuberculosis* infections in mice.

Table I

| Compound of Example | Percent of Compound in Diet | Alive/Total Mice Tested 28 Days After Infection |
| --- | --- | --- |
| 9 | 0.05 | 5/5 |
|  | 0.0125 | 2/5 |
| 10 | 0.05 | 4/5 |
|  |  | 3/5 |
| 11 | 0.05 | 5/5 |
|  |  | 3/5 |
| 12 | 0.0125 | 2/5 |
|  | 0.5 | 2/5 |
| 13 | 0.0125 | 2/5 |
|  | 0.05 | 3/5 |
| 14 | 0.05 | 2/5 |
|  |  | 4/5 |
| 15 | 0.05 | 4/5 |
|  |  | 4/5 |
| 16 | 0.05 | 2/5 |
|  |  | 4/5 |
| 17 | 0.05 | 2/5 |
|  |  | 2/5 |
| 18 | 0.05 | 2/5 |
| 19 | 0.0125 | 2/5 |
|  | 0.05 | 5/5 |
|  |  | 4/5 |
| 20 | 0.05 | 5/5 |
|  |  | 4/5 |
| 21 | 0.0125 | 2/5 |
|  | 0.05 | 2/5 |
| 22 | 0.05 | 4/5 |
|  |  | 3/5 |
| 23 | 0.05 | 4/5 |
|  |  | 4/5 |
| 24 | 0.05 | 4/5 |

Table I-continued

| Compound of Example | Percent of Compound in Diet | Alive/Total Mice Tested 28 Days After Infection |
| --- | --- | --- |
| 25 | 0.05 | 3/5 4/5 |
| 26 | 0.05 | 4/5 5/5 |
| 27 | 0.05 | 4/5 |
| 28 | 0.05 | 5/5 |
| 29 | 0.0125 | 5/5 4/5 |
|    | 0.05 | 2/5 5/5 |
| 30 | 0.0125 | 5/5 3/5 |
|    | 0.05 | 3/5 5/5 |
| 31 | 0.0125 | 5/5 5/5 |
|    | 0.05 | 5/5 2/5 |
| 32 | 0.05 | 4/5 4/5 |
| 33 | 0.0125 | 4/5 5/5 |
|    | 0.05 | 4/5 5/5 |
| 34 | 0.05 | 5/5 2/5 |
| 35 | 0.0125 | 4/5 2/5 |
|    | 0.05 | 2/5 5/5 |
| 36 | 0.0125 | 3/5 |
|    | 0.05 | 3/5 3/5 |
| 37 | 0.05 | 3/5 |
| 38 | 0.05 | 3/5 |
| 39 | 0.0125 | 4/5 |
|    | 0.05 | 2/5 |
| 40 | 0.05 | 2/5 2/5 |
| 41 | 0.0125 | 2/5 2/5 |
|    | 0.05 | 5/5 4/5 |
| 42 | 0.0125 | 4/5 4/5 |
|    | 0.05 | 5/5 5/5 |
| 43 | 0.0125 | 3/5 3/5 |
| 44 | 0.05 | 2/5 |
| 45 | 0.05 | 3/5 3/5 |
| 46 | 0.0125 | 4/5 |
|    | 0.05 | 5/5 |
| 47 | 0.05 | 2/5 |
| 48 | 0.05 | 5/5 |
| 49 | 0.05 | 2/5 |
| 50 | 0.05 | 5/5 |
|    | 0.0125 | 2/5 |
| 51 | 0.05 | 4/5 |
| 52 | 0.05 | 5/5 |
|    | 0.0125 | 3/5 |
| 53 | 0.05 | 2/5 |
| 54 | 0.05 | 2/5 |
| 55 | 0.05 | 3/5 |

Compositions containing as the active component a 2-(1,3-diazacycloalkenyl)-2-hydrazone of a substituted chalcone of this invention may be administered to warm-blooded animals orally, or parenterally if desired, and when so administered, may be considered as an agent for the therapeutic treatment of tuberculosis infections in daily doses ranging from about 2 mg. to about 100 mg. per kilogram of body weight. The dose regimen can be adjusted to provide optimum therapeutic response. Thus, for example, several smaller doses may be administered daily, or the dose may be reduced or increased proportionately as indicated by the requirements or the particular therapeutic situation.

The active compounds of this invention may be incorporated with pharmaceutically acceptable carriers such as excipients and used, for example, in the form of tablets, dragees, capsules, suppositories, liquids, elixirs, emulsions, suspensions or the like. Such compositions and preparations should contain at least 5% active component. The percentage in the compositions and preparations may, of course, be varied and may conveniently be between 10 and 60% or more of the weight of the unit. The amount of compound in such therapeutically useful compositions or preparations is such that a suitable dosage will be obtained. Preferred compositions or preparations according to the present invention are prepared so that a dosage unit form contains between about 10 and about 500 mg. of the active compound. In addition to the therapeutic compound there may be present excipients, binders, fillers and other therapeutically inert ingredients necessary in the formulation of the desired pharmaceutical preparation.

SPECIFIC DISCLOSURE

The following examples describe the preparation of intermediates and final products of this invention.

EXAMPLE 1

Preparation of Starting Material
1,4,5,6-Tetrahydro-2-hydrazino-pyrimidine hydroiodide A 25.8 gm. (0.1 mole) portion of 2-methylthio-1,4,5,6-tetrahydropyrimidine hydroiodide in 200 ml. of ethanol is stirred and heated in a steam bath with 6 ml. (0.12 mole) of hydrazine hydrate. The mixture is stirred at reflux for 2½ hours. The mixture is cooled to −10°C. and ether is added. The precipitate is collected, washed wiith 200 ml. of ether and dried at 60°C. under reduced pressure. Yield 22.1 gm., melting point 174°–175°C.

Analysis calculated for $C_4H_{10}N_4 \cdot HI$: C, 19.84; H, 4.56; N, 23.14; I, 52.43. Found: C, 19.93; H, 4.55; N, 23.22; I, 53.35.

EXAMPLE 2

Preparation of Starting Material
2-Hydrazino-2-imidazoline hydrochloride

A 33.0 gm. (0.135 mole) portion of 2-methylthio-2-imidazoline hydroiodide is dissolved in 300 ml. of water and treated with 8 ml. (0.16 mole) of hydrazine hydrate. The mixture is stirred at room temperature for 20 hours and then taken to dryness under reduced pressure. The residue is dissolved in 250 ml. of water and again taken to dryness under reduced pressure. The residue is redissolved in 250 ml. of water and added to a mixture of 250 ml. of water, 25 ml. of concentrated hydrochloric acid and 25 gm. of silver oxide. The resulting mixture is stirred on a steam bath for 4 hours and then filtered. The filtrate is reduced to dryness under reduced pressure. The residue is dissolved in 300 ml. of ethanol and 20 ml. of water at the boil, clarified and cooled at −10°C. The precipitate is collected, washed with ethanol and ether and dried at 60°C. and then 110°C. under reduced pressure. Yield 11.6 gm., melting point 177°–180°C.

Analysis calculated for $C_3H_8N_4 \cdot HCl$: C, 26.38; H, 6.64; N, 41.02; Cl, 25.96. Found: C, 26.06; H, 6.38; N, 40.13; Cl, 25.59.

EXAMPLE 3

Preparation of Starting Material 2-Hydrazino-4,5,6,7-tetrahydro-1H-1,3-diazepine hydroiodide A 40.8 gm. (0.15 mole) portion of 2-methylthio-4,5,6,7-tetrahydro-1H-1,3-diazepine hydroiodide in 150 ml. of ethanol is treated with 10 ml. (0.2 mole) of hydrazine hydrate. The solution is stirred at reflux for 3 hours, clarified while hot and then cooled at $-10°C$. overnight. A 200 ml. portion of ether is added and the mixture is cooled at $-10°C$. The precipitate is collected, washed with ether and dried at 60°C. under reduced pressure. Yield 20.5 gm., melting point 133°–135°C. Analysis calculated for: $C_5H_{12}N_4 \cdot HI$: C, 23.45; H, 5.12; N, 21.88; I, 49.56. Found: C, 22.85; H, 4.96; N, 21.90; I, 50.35.

EXAMPLE 4

Preparation of Starting Material 2-Hydrazino-4-methyl-2-imidazoline dihydrochloride Eighty grams of 4-methyl-2-methylthio-2-imidazoline hydroiodide, 20 ml. of 100% hydrazine hydrate and 250 ml. of ethanol are combined and heated under reflux for 16 hours. Removal of solvent leaves a glassy solid which resists attempts at crystallization. Conversion to the hydrochloride salt is similarly unsuccessful. However, solution of the latter salt in n-propanol followed by addition of an equivalent of anhydrous hydrogen chloride in the same solvent gives the dihydrochloride salt, melting at 128°–131°C.

Analysis calculated for $C_4H_{10}N_4 \cdot 2HCl$: C, 25.68; H, 6.47; N, 29.95; Cl, 37.90. Found: C, 24.96; H, 6.25; N, 30.04; Cl, 37.39.

EXAMPLE 5

Preparation of Starting Material 2-Hydrazino-1,4,5,6-tetrahydro-5,5-dimethyl pyrimidine hydrobromide A 25.3 gm. (0.1 mole) portion of 5,5-dimethyl-2-methylthio-1,4,5,6-tetrahydropyrimidine hydrobromide in 100 ml. of n-propanol is treated with 5.0 gm. (0.1 mole) of hydrazine hydrate. The solution is stirred and heated on a steam bath for 4 hours and clarified while hot. The product crystallizes on the filter paper. This is extracted with 100 ml. of boiling propanol and both filtrates are cooled at $-10C$. The precipitates are collected, washed with cold propanol and 200 ml. of ether and dried at 60°C. under reduced pressure. Yield 15.8 gm., melting point 234°–235°C.

Analysis calculated for $C_6H_{14}N_4 \cdot HBr$: C, 32.30; H, 6.78; N, 25.11; Br, 35.81. Found: C, 32.37; H, 6.72; N, 25.33; Br, 35.21.

EXAMPLE 6

Preparation of Starting Material 2-Hydrazino-2-imidazoline hydrobromide

A 306 gm. (3.0 mole) portion of 2-imidazolidinethione is heated to reflux in 1200 ml. of ethanol and 250 ml. (365 gm.) (3.35 mole) of ethyl bromide. The solid slowly dissolves over a period of 4½ hours. A 151 gm. (3.0 + mole) portion of hydrazine hydrate is added in portions with some heating. The mixture is allowed to stand overnight. Crystals which form during the reaction and are dissolved by the addition of about 125 ml. of water, reform in the cooled mixture. The supernatant is filtered and concentrated to give white crystals. The solid is dissolved in 1 liter of hot methanol, filtered, concentrated and cooled to give white crystals which are washed with propanol and ether.

Yield 404.2 gm., melting point 184.5°–185.5°C. Analysis calculated for $C_3H_8N_4 \cdot HBr$: C, 19.90; H, 5.01; N, 30.95; Br, 44.14. Found: C, 19.79; H, 4.88; N, 31.56; Br, 44.66.

EXAMPLE 7

Preparation of Starting Material 2-Hydrazino-1,4,5,6-tetrahydropyrimidine hydrochloride A 35 gm. (0.3 mole) portion of 2-mercapto-1,4,5,6-tetrahydropyrimidine in 500 ml. of ethanol is stirred as 30 ml. of methyl iodide is added. The mixture is refluxed with stirring for 8 hours. A 25 ml. portion of concentrated hydrochloric acid and 48 gm. of silver chloride are added and the mixture is stirred at reflux for 1 hour and then allowed to stand at room temperature for 2½ days. The mixture is refluxed for 5 more hours, clarified and the filtrate is reduced to an oil under reduced pressure. The oil is dissolved in 100 ml. of boiling isopropanol and then cooled at $-10°C$. A 300 ml. portion of acetone is added and the mixture is kept at $-10°C$. The precipitate which forms is collected washed with acetone and dried at 60°C. under reduced pressure. This solid is dissolved in 150 ml. of ethanol, treated with 8 ml. (0.16 mole) of hydrazine hydrate and stirred at reflux for 6 hours. The mixture is filtered hot and cooled at $-10°C$. The mixture is diluted with 150 ml. of ether and stored at $-10°C$. The precipitate which forms is collected, washed with 150 ml. of ether and dried under reduced pressure at 60°C.

Yield 17.9 gm., melting point 191°–192°C. Analysis calculated for $C_4H_{10}N_4 \cdot HCl$: C, 31.90; H, 7.36; N, 37.20; Cl, 23.54. Found: C, 32.14; H, 7.38; N, 37.98; Cl, 22.89.

EXAMPLE 8

Preparation of Starting Material 2-Hydrazino-4,5,6,7-tetrahydro-1H-1,3-diazepine hydrochloride A 38.5 gm. (0.14 mole) portion of 2-methylthio-4,5,6,7-tetrahydro-1H-1,3-diazepine hydroiodide is slurried in a mixture of 500 ml. of water and 40 gm. (0.3 mole) of silver chloride. The mixture is stirred on a steam bath for 16 hours. The mixture is filtered and the filtrate is taken to dryness under reduced pressure. The residue is dissolved in 150 ml. of ethanol to which is added 7 ml. (0.14 mole) of hydrazine hydrate. The mixture is refluxed for 3 hours, clarified and cooled at $-10°C$. A 150 ml. portion of ether is added. The precipitate which forms is collected, washed with 150 ml. of ether and dried at 60°C. under reduced pressure yielding 19.4 gm., melting point 192°–193°C.

Analysis calculated for $C_5H_{12}N_4 \cdot HCl$: C, 36.47; H, 7.96; N, 34.03; Cl, 21.53. Found: C, 36.23; H, 8.07; N, 34.05; Cl, 21.49.

EXAMPLE 9

Preparation of the 2-Imidazolin-2-yl-hydrazone of 4,4'-Dichlorochalcone hydrobromide A 5.55 gm. (0.02 mole) portion of 4,4'-dichlorochalcone, prepared as described by Straus and Ackermann, Ber. 42, 1802 (1909), 3.60 gm. (0.02 mole) of 2- hydrazino-2-imidazoline hydrobromide and 3 drops of hydrobromic acid in 100 ml. of n-propanol are boiled for one hour and then allowed to stand at room temperature overnight. The crystals which separate are collected by filtration and washed with ether. More crystals are collected by concentrating the filtrate. The combined crystals are recrystallized from 400 ml. of ethanol to yield 7.08 gm. of white crystalline product, melting point 226.5°–227.5°C.

Analysis calculated for $C_{18}H_{16}N_4Cl_2 \cdot HBr$: C, 49.11; H, 3.89; N, 12.73; Cl, 16.11; Br, 18.15. Found: C, 48.91; H, 4.03; N, 12.96; Cl, 15.49; Br, 18.63.

EXAMPLE 10

Preparation of the 2-Imidazolin-2-ylhydrazone of 3-(4-Chlorophenyl)-2'-acrylonaphthone hydrobromide A 2.9 gm. (0.01 mole) portion of 3-(4-chlorophenyl)-2'-acrylonaphthone, 1.8 gm. (0.01 mole) of 2-hydrazino-2-imidazoline hydrobromide and 3 drops of 48% hydrobromic acid in 100 ml. of propanol are refluxed for 6 hours, clarified while hot and cooled at −10°C. for 3 hours. The precipitate which forms is collected, washed with 50 ml. of propanol and then with 200 ml. of ether and finally dried at 60°C. under reduced pressure, yielding 2.7 gm., of product, melting point 214°–6°C.

Analysis calculated for $C_{22}H_{19}N_4Cl \cdot HBr$: C, 57.97; H, 4.42; N, 12.29; Cl, 7.78; Br, 17.53. Found: C, 57.96; H, 4.86; N, 12.09; Cl, 8.11; Br, 18.26.

The starting material, 3-(4-chlorophenyl)-2'-acrylonaphthone, is prepared by the reaction of 4-chlorobenzaldehyde and 2-acetonaphthone in ethanol solution in the presence of aqueous sodium hydroxide. After recrystallization from 2-methoxyethanol, it melts at 170°C.–171°C.

EXAMPLE 11

Preparation of the 2-Imidazolin-2-ylhydrazone of 4,4'-Dichloro-β-methylchalcone hydrobromide A 1.80 gm. (0.0062 mole) portion of 4,4'-dichloro-β-methylchalcone, prepared as described by Carrie and Rochard, Compt. rend. 257, 2849 (1963), 1.20 gm. (0.0066 mole) of 2-hydrazino-2-imidazoline hydrobromide and 3 drops of hydrobromic acid in 100 ml. of ethanol are heated to boiling for 2 hours during which time the ethanol is replaced with n-propanol and the volume is reduced to 30 ml. The mixture is cooled and the white crystals which form are collected and dried yielding 2.0 gm. of the product, melting point 248°–249°C.

Analysis calculated for $C_{19}H_{18}N_4Cl_2 \cdot HBr$: C, 50.25; H, 4.22; N, 12.33; Cl, 15.61; Br, 17.59. Found: C, 49.92; H, 4.14; N, 12.52; Cl, 14.62; Br, 18.07.

EXAMPLE 12

Preparation of the 2-Imidazolin-2-ylhydrazone of 4'-Chloro-2,3,5,6-tetramethylchalcone hydrobromide A 4.45 gm. (0.0149 mole) portion of 4'-chloro-2,3,5,6-tetramethylchalcone, a 3.0 gm. (0.0166 mole) portion of 2-hydrazino-2-imidazoline hydrobromide and 5 drops of hydrobromic acid in 50 ml. of n-propanol are heated to boiling. The solid starting materials dissolve just prior to the boiling point and then a white solid gradually comes out of solution. After about 20 minutes boiling with the addition of 20 ml. of n-propanol the hot solution is filtered yielding off-white crystals. Further boiling of the filtrate yields additional crystals. The crystals are washed with n-propanol and benzene and then dried, yielding 5.40 gm., melting point 254°–256°C.

Analysis calculated for $C_{22}H_{25}N_4Cl \cdot HBr$: C, 57.22; H, 5.67; N, 12.13; Cl, 7.67; Br, 17.30. Found: C, 56.89; H, 5.70; N, 12.39; Cl, 7.94; Br, 18.17.

The starting material 4'-chloro-2,3,5,6-tetramethylchalcone, is prepared by the reaction of 4'-chloroacetophenone and 2,3,5,6-tetramethylbenzaldehyde in ethanol solution in the presence of aqueous sodium hydroxide. After recrystallization from a benzene-hexane mixture, it melts at 133°–133.5°C.

EXAMPLE 13

Preparation of the 2-Imidazolin-2-ylhydrazone of 4'-Chloro-3-methylchalcone hydrobromide A 7.65 gm. (0.03 mole) portion of 4'-chloro-3-methylchalcone, 5.70 gm. (0.031 mole) of 2-hydrazino-2-imidazoline hydrobromide and 5 drops of hydrobromic acid are dissolved in 100 ml. of n-propanol and boiled for 30 minutes. The mixture is concentrated to about 30 ml. and 30 ml. of ether is added. The crystals which form are washed with n-propanol and dried, yielding 11.86 gm. of product, melting point 217°–219°C. Analysis calculated for $C_{19}H_{19}N_4Cl \cdot HBr$: C, 54.37; H, 4.80; N, 13.35; Cl, 8.44; Br, 19.04. Found: C, 53.89; H, 4.79; N, 13.52; Cl, 8.18; Br, 19.61.

The starting material, 4'-chloro-3-methylchalcone, is prepared by the reaction of 4'-chloroacetophenone and 3-methylbenzaldehyde in methanol solution in the presence of aqueous sodium hydroxide. After recrystallization from benzene, it melts at 119°–120°C.

EXAMPLE 14

Preparation of the 2-Imidazolin-2-ylhydrazone of 2,4,4'-Trichlorocalcone hydrobromide A 6.2 gm. (0.02 mole) portion of 2,4,4'-trichlorochalcone, 3.7 gm. (0.02 mole) of 2-hydrazino-2-imidazoline hydrobromide and 8 drops of 48% hydrobromic acid are dissolved in 150 ml. of n-propanol and stirred at reflux temperature. A heavy precipitate forms in about 30 minutes. Some n-propanol is added and the mixture is stirred at reflux for 16 hours. The mixture is cooled at −10°C., the precipitate is collected and washed with n-propanol and ether and air dried. The product is recrystallized from 400 ml. of hot ethanol and cooled at −10°C. The precipitate is collected, washed with a little ethanol and then ether, and dried at 60°C. under reduced pressure.

Yield 2.8 gm., melting point 248°–249°C. Analysis calculated for $C_{18}H_{15}N_4Cl_3 \cdot HBr$: C, 45.55; H, 3.40; N, 11.81; Cl, 22.41; Br, 16.84. Found: C, 45.50; H, 3.42; N, 11.87; Cl, 22.02; Br, 17.88.

The starting material, 2,4,4'-trichlorochalcone, is prepared by the reaction of 2,4-dichlorobenzaldehyde and 4'-chloroacetophenone in ethanol solution in the presence of aqueous sodium hydroxide. After recrystallization from 2-methoxyethanol, the compound melts at 115°–116°C.

EXAMPLE 15

Preparation of the 2-Imidazolin-2-ylhydrazone of 4-Bromo-4'-chlorochalcone hydrobromide A 3.3 gm. (0.01 mole) portion of 4-bromo-4'-chlorochalcone, commercially available from the Aldrich Chemical Company, 1.9 gm. (0.01 mole) of 2-hydrazino-2-imidazoline hydrobromide and 5 drops of 48% hydrobromic acid are dissolved in 100 ml. of n-propanol. The solution is stirred at reflux temperature for 7 hours and then cooled at −10°C. The precipitate, which forms slowly, is collected, washed with n-propanol and ether and air dried. The product is recrystallized from 100 ml. of n-propanol, clarified, cooled at −10°C. The precipitate is collected, washed with a little propanol and ether and then dried at 60°C. under reduced pressure yielding 2.3 gm., melting point 223°–225°C.

Analysis calculated for $C_{18}H_{16}N_4BrCl \cdot HBr$: C, 44.61; H, 3.54; N, 11.56. Found: C, 44.74; H, 3.73; N, 11.81.

EXAMPLE 16

Preparation of the 2-Imidazolin-2-ylhydrazone of 4-Chloro-4'-ethoxychalcone hydrobromide An 8.6 gm. (0.03 mole) portion of 4-chloro-4'-ethoxychalcone, 5.5 gm. (0.03 mole) of 2-hydrazino-2-imidazoline hydrobromide and 7 ml. of 48% hydrobromic acid in 200 ml. of n-propanol are refluxed for 8 hours. The solution is cooled to −10°C. The precipitate which forms is collected, washed with n-propanol and ether and dried at 60°C. under reduced pressure. The product is recrystallized from 100 ml. of n-propanol and cooled at −10°C. The precipitate is collected, washed with cold n-propanol and ether and dried at 60°C. under reduced pressure, yielding 5.9 gm., melting point 216°–217°C.

Analysis calculated for $C_{20}H_{21}N_4OCl \cdot HBr$: C, 53.41; H, 4.93; N, 12.46; Cl, 7.88; Br, 17.77. Found: C, 53.38; H, 5.05; N, 12.59; Cl, 7.81; Br, 18.11.

The starting material, 4-chloro-4'-ethoxychalcone, is prepared by the reaction of 4'-ethoxyacetophenone and 4-chlorobenzaldehyde in ethanol solution in the presence of aqueous sodium hydroxide. After recrystallization from 2-methoxyethanol, it melts at 141°–142°C.

EXAMPLE 17

Preparation of the 2-Imidazolin-2-ylhydrazone of 4'-Chloro-2,5-dimethylchalcone hydrobromide A 5.4 gm. (0.02 mole) portion of 4'-chloro-2,5-dimethylchalcone, 3.65 gm. (0.02 + mole) of 2-hydrazino-2-imidazoline hydrobromide and 5 drops of hydrobromic acid in 50 ml. of n-propanol is boiled for 10 minutes. The crystals which form are collected by filtration and washed with two 15 ml. portions of ethanol yielding 7.39 gm., melting point 257.5°–258.5°C.

Analysis calculated for $C_{20}H_{21}N_4Cl \cdot HBr$: C, 55.38; H, 5.11; N, 12.92. Found: C, 55.03; H, 5.03; N, 12.90.

The starting material, 4'-chloro-2,5-dimethylchalcone is prepared by the reaction of 2,5-dimethylbenzaldehyde and 4'-chloroacetophenone in methanol solution in the presence of aqueous sodium hydroxide. After recrystallization from a benzene-hexane mixture, it melts at 81°–82°C.

EXAMPLE 18

Preparation of the 2-Imidazolin-2-ylhydrazone of 3-(9-anthryl)-4'-chloro-acrylophenone hydrobromide A 6.8 gm. (0.02 mole) portion of 3-(9-anthryl)-4'-chloroacrylophenone, 3.6 gm. (0.02 mole) of 2-hydrazino-2-imidazoline hydrobromide and 5 drops of hydrobromic acid are added to 100 ml. of propanol. The mixture is boiled for about 20 minutes and then allowed to stand overnight. A yellow solid forms. The mixture is boiled for 15 minutes and then filtered while warm to yield a yellow solid. This solid is washed with ethanol. Further boiling of the filtrate yielded yellow needles. The combined product is recrystallized by dissolving in boiling methanol (400 ml.) filtering and concentrating. The yield is 6.56 gm., melting point 261°–263°C.

Analysis calculated for $C_{26}H_{21}N_4Cl \cdot HBr$: C, 61.74; H, 4.38; N, 11.07; Cl, 7.01; Br, 15.79. Found: C, 61.47; H, 4.43; N, 11.08; Cl, 7.12; Br, 15.95.

The starting material, 3-(9-anthryl)-4'-chloroacrylophenone, is prepared by the reaction of 9-anthraldehyde and 4'-chloroacetophenone in ethanol solution in the presence of aqueous sodium hydroxide. After recrystallization from a benzene-hexane mixture, it melts at 133.5°–135.5°C.

EXAMPLE 19

Preparation of the 4,5,6,7-Tetrahydro-1H-1,3-diazepin-2-yl-hydrazone of 4,4'-Dichlorochalcone hydrochloride A 3.1 gm. portion of 2-hydrazino-4,5,6,7-tetrahydro-1H-1,3-diazepin hydroiodide, 3.5 gm. of 4,4'-dichlorochalcone, 3.5 gm. of silver chloride and 7 drops of concentrated hydrochloric acid are added to 100 ml. of n-propanol. The mixture is stirred at reflux for 9½ hours, clarified while hot and cooled at −10°C. overnight. The precipitate is collected, washed with cold n-propanol by 25 ml. of water and 100 ml. of ether and then air dried. The product is recrystallized from 100 ml. of isopropanol, cooled at −10°C., collected and washed with 15 ml. of cold isopropanol, 100 ml. of ether and dried at 60°C. under reduced pressure. The yield is 1.1 gm., melting point 221°–223°C.

Analysis calculated for $C_{20}H_{20}N_4Cl_2 \cdot HCl$: C, 56.68; H, 5.00; N, 13.22; Cl, 25.10. Found: C, 57.35; H, 5.13; N, 13.27; Cl, 24.43.

EXAMPLE 20

Preparation of the 2-Imidazolin-2-ylhydrazone of 4'-Chloro-4-phenylchalcone hydrobromide A mixture of 6.4 gm. (0.02 mole) of 4'-chloro-4-phenylchalcone [prepared as described by Kozlov, et al., Chem. Abst., 58, 7858d (1963)], 3.62 gm. (0.02 mole) of 2-hydrazino-2-imidazoline hydrobromide and 3 drops of hydrobromic acid in 125 ml. of n-propanol are stirred and heated to boiling. Heating is continued until the solution is concentrated to about 100 ml. The mixture is cooled and the pale yellow precipitate is collected by filtration, washed with n-propanol and dried.

Yield 8.0 gm., melting point 247°–248°C. Analysis calculated for $C_{24}H_{21}N_4Cl \cdot HBr$: C, 59.83; H, 4.60; N, 11.67. Found: C, 60.32; H, 4.73; N, 11.90.

EXAMPLE 21

Preparation of the 2-Imidazolin-2-ylhydrazone of 4-Chloro-4'-phenylchalcone hydrobromide A mixture of 6.2 gm. (0.02 mole) of 4-chloro-4'-phenylchalcone [prepared as described by Kushwaha, et al., Chem. Abst., 66, 65236p (1967)], 3.62 gm. (0.02 mole) of 2-hydrazino-2-imidazoline hydrobromide and 3 drops of hydrobromic acid in 125 ml. of n-propanol is stirred and heated to boiling. Heating is continued until the volume is reduced to 50–60 ml. The mixture is cooled. The product is collected by filtration, washed with n-propanol and dried yielding 8.0 gm., melting point 247°–248°C.

EXAMPLE 22

Preparation of the (1,4,5,6-Tetrahydro-2-pyrimidinyl)hydrazone of 4,4'-Dichlorochalcone hydrochloride A mixture of 8.3 gm. (0.03 mole) of 4,4'-dichlorochalcone, 4.8 gm. (0.03 + mole) of 2-hydrazino-1,4,5,6-tetrahydro-pyrimidine hydrochloride and 8 drops of concentrated hydrochloric acid in 100 ml. of n-propanol is stirred at reflux for 16 hours. The solution is clarified and cooled at −10°C. A small portion is diluted with ether until a precipitate forms. This slurry is added to the balance of the n-propanol solution and maintained at −10°C. for 5 hours. The precipitate is collected and washed with 20 ml. of n-propanol.

Yield 6.8 gm., melting point 224°–226°C. Analysis calculated for $C_{19}H_{18}N_4Cl_2$ . HCL: C, 55.69; H, 4.67; N, 13.67; Cl, 25.96. Found: C, 55.72; H, 4.75; N, 13.63; Cl, 25.74.

EXAMPLE 23

Preparation of the 2-Imidazolin-2-ylhydrazone of 4-Chloro-4'-(trifluoromethyl)chalcone hydrobromide A mixture of 6.2 gm. (0.02 mole) of 4-chloro-4'-(trifluoromethyl)chalcone, 3.62 gm. (0.02 mole) of 2-hydrazino-2-imidazoline hydrobromide and 3 drops of hydrobromic acid in 150 ml. of n-propanol is boiled for 2 hours. The mixture is allowed to stand at room temperature. The precipitate is collected by filtration and washed with n-propanol.

Yield 7.8 gm., melting point 270°C., resolidifies then remelts at 315°C. Analysis calculated for $C_{19}H_{17}N_4F_3Cl$ . HBr: C, 48.17; H, 3.62; N, 11.83. Found: C, 48.36; H, 3.65; N, 11.99.

The starting material, 4-chloro-4'-trifluoromethyl chalcone, is prepared by the reaction of 4-chlorobenzaldehyde and 4'-trifluoromethylacetophenone in methanol solution in the presence of aqueous sodium hydroxide. The precipitated solid is collected, washed with methanol and water, and dried, melting point 131°–133°C.

EXAMPLE 24

Preparation of the 2-Imidazolin-2-ylhydrazone of 4,4'-bis(trifluoromethyl)chalcone hydrobromide A mixture of 6.9 gm. (0.02 mole) of 4,4'-bis(trifluoromethyl)chalcone, 3.62 gm. (0.02 mole) of 2-hydrazino-2-imidazoline hydrobromide and 3 drops of hydrobromic acid in 150 ml. of n-propanol is boiled for 2 hours and then cooled. The precipitate is collected, washed with n-propanol and dried. Yield 5.5 gm; melting at about 270°C.; resolidifying and then melting at about 300°C.

Analysis calculated for $C_{20}H_{16}N_4F_6$ . HBr: C, 47.35; H, 3.38; N, 11.05. Found: C, 47.27; H, 3.18; N, 10.92.

The starting material, 4,4'-bis(trifluoromethyl)-chalcone is prepared by the reaction of 4'-trifluoromethylacetophenone and 4-trifluoromethylbenzaldehyde in methanol solution in the presence of aqueous sodium hydroxide. The precipitated solid is collected, washed with methanol and water, and dried, melting point 94°–96°C.

EXAMPLE 25

Preparation of the (1,4,5,6-Tetrahydro-2-pyrimidinyl)hydrazone of 4,4'-Dichloro-β-methylchalcone hydrochloride A mixture of 4.4 gm. (0.015 mole) of 4,4'-dichloro-β-methylchalcone and 2.25 gm. (0.015 mole) of 2-hydrazino-1,4,5,-6-tetrahydropyrimidine hydrochloride in 50 ml. of n-propanol containing 5 drops of concentrated hydrochloric acid is boiled for 1 hour. The solvent is replaced with methyl cellosolve and boiling is continued for 1 hour. The mixture is cooled. The precipitate is collected and recrystallized from methanolethanol, yielding 2.35 gm., melting point 252°–258°C. A second crop melts at 259°–262°C. These crops are combined and dissolved in 40 ml. of hot methanol and 2.2 ml. of 10N sodium hydroxide. A 15 ml. portion of water is added. The precipitate is collected, washed with water and 10 ml. of methanol and dried yielding 4.29 gm., melting point 145°–146.5°C.

This 4.29 gm. is dissolved in 80 ml. of chloroform and 6.7 N hydrochloric acid in 2-propanol is added. The white crystals are collected and washed with chloroform and ethanol yielding 4.06 gm. of the title product, melting point 254°–255°C.

Analysis calculated for $C_{20}H_{20}N_4Cl_2$ . HCl: C, 56.69; H, 4.99; N, 13.22; Cl, 25.09. Found: C, 56.55; H, 5.16; N, 13.36; Cl, 24.85.

EXAMPLE 26

Preparation of the 2-Imidazolin-2-ylhydrazone of 4'-Chloro-4-(trifluoromethyl)chalcone hydrobromide A mixture of 6.2 gm. (0.02 mole) of 4'-chloro-4-(trifluoromethyl)chalcone, 3.62 gm. (0.02 mole) of 2-hydrazino-2-imidazoline hydrobromide and 3 drops of hydrobromic acid in 150 ml. of n-propanol is boiled for 2 hours and then allowed to stand for several days. The solid which forms is washed with n-propanol, yield 5.1 gm., melting point 250°–253°C.

Analysis calculated for $C_{19}H_{17}N_4ClF_3$ . HBr: C, 48.17; H, 3.62; N, 11.83. Found: C, 47.64; H, 3.57; N, 11.84.

The starting material, 4'-chloro-4-trifluoromethyl chalcone, is prepared by the reaction of 4'-chloroacetophenone and 4-trifluoromethylbenzaldehyde in methanol solution containing aqueous sodium hydroxide. The precipitate is collected, washed with methanol and water, and dried, melting point 110°–112°C.

EXAMPLE 27

Preparation of the 2-Imidazolin-2-ylhydrazone of 4'-Bromo-4-chlorochalcone hydrobromide A mixture of 9.6 gm. (0.03 mole) of 4'-bromo-4-chlorochalcone, 6.0 gm. (0.033 mole) of 2-hydrazino-2-imidazoline hydrobromide and 12 drops of 48% hydrobromic acid in 200 ml. of n-propanol is stirred at reflux for 8 hours, clarified while hot and then cooled at −10°C. The precipitate is collected, washed with 75 ml. of cold n-propanol and then 200 ml. of ether and dried at 60°C. under reduced pressure. Yield 9.1 gm., melting point 223°–224°C.

Analysis calculated for $C_{18}H_{16}N_4BrCl \cdot HBr$: C, 44.61; H, 3.54; N, 11.56; Cl, 7.32; Br, 32.98. Found: C, 44.55; H, 3.53; N, 11.56; Cl, 7.53; Br, 32.62.

The starting material, 4′-bromo-4-chlorochalcone, is prepared by the reaction of 4′-bromoacetophenone and 4-chlorobenzaldehyde is ethanol solution in the presence of aqueous sodium hydroxide. After recrystallization from 2-methoxyethanol, the compound melts at 167°–168°C.

EXAMPLE 28

Preparation of the 2-Imidazolin-2-ylhydrazone of 4′-Chloro-3-(2-naphthyl)-acrylophenone hydrobromide A mixture of 4.5 gm. (0.015 mole) of 4′-chloro-3-(2-naphthyl)acrylophenone, 3.0 gm. (0.017 mole) of 2-hydrazino-2-imidazoline hydrobromide and 8 drops of 48% hydrobromic acid in 100 ml. of n-propanol is stirred at reflux for 8 hours and then clarified while hot. The precipitate is washed with 50 ml. of cold n-propanol and then 100 ml. of ether and dried at 60°C. under reduced pressure.

Yield 3.1 gm., melting point 235°–236°C. Analysis calculated for $C_{22}H_{19}N_4Cl \cdot HBr$: C, 57.97; H, 4.42; N, 12.29; Br, 17.53; Cl, 7.78. Found: C, 57.91; H, 4.43; N, 12.27; Br, 16.91; Cl, 7.90.

The starting material, 4′-chloro-3-(2-naphthyl)acrylophenone, is prepared by the reaction of 4′-chloroacetophenone and 2 . solution in the presence of aqueous sodium hydroxide. After recrystallization from 2-methoxyethanol, the compound melts at 183°–184°C.

EXAMPLE 29

Preparation of the 4,5,6,7-Tetrahydro-1H-1,3-diazepin-2-yl-hydrazone of 4,4′-Dichloro-β-methylchalcone hydrochloride A mixture of 4.4 gm. (0.015 mole) of 4,4′-dichloro-β-methylchalcone, 2.5 gm. (0.015 + mole) of 2-hydrazino-4,5,6,7-tetrahydro-1H-1,3-diazepine hydrochloride and 2 drops of concentrated hydrochloric acid in 50 ml. of n-propanol is boiled for 1 hour. Ether is added and a precipitate forms. This material is recrystallized by dissolving in chloroform and adding benzene and then concentrating to remove most of the chloroform. The product is recovered as a white solid, yield 4.5 gm., melting point 157°–160°C.

Analysis calculated for $C_{21}H_{22}N_4Cl_2 \cdot HCl$: C, 57.62; H, 5.29; N, 12.80; Cl, 24.29. Found: C, 57.58; H, 5.36; N, 12.68; Cl, 24.77.

EXAMPLE 30

Preparation of the 4,5,6,7-Tetrahydro-1H-1,3-diazepin-2-ylhydrazone of 4′-Chloro-4-phenylchalcone hydrochloride n-propanolate A mixture of 6.2 gm. (0.02 mole) of 4′-chloro-4-phenylchalcone, 3.30 gm. (0.02 mole) of 2-hydrazino-4,5,6,7-tetrahydro-1H-1,3-diazepine hydrochloride and 3 drops of concentrated hydrochloric acid in 100 ml. of n-propanol is boiled for 1 hour and then stored overnight at 5°C. The product is collected by filtration, yield 8.0 gm., melting point 150°–153°C.

Analysis calculated for $C_{26}H_{25}N_4Cl \cdot HCl \cdot C_3H_8O$: C, 66.33; H, 6.53; N, 10.66. Found: C, 66.56; H, 6.84; N, 10.38.

EXAMPLE 31

Preparation of 4,5,6,7-Tetrahydro-1H-1,3-diazepin-2-ylhydrazone of 4′-Chloro-4-(trifluoromethyl)chalcone hydrochloride A mixture of 6.2 gm. (0.02 mole) of 4′-chloro-4-(trifluoromethyl)chalcone, 3.3 gm. (0.02 mole) of 2-hydrazino-4,5,6, 7-tetrahydro-1H-1,3-diazepine hydrochloride and 3 drops of concentrated hydrochloric acid in 75 ml. of n-propanol is boiled for 1 hour and cooled overnight. The product is collected by filtration, yield 3.3 gm., melting point 220°–222°C.

Analysis calculated for $C_{21}H_{21}N_4Cl_2F_3 \cdot HCl$: C, 55.15; H, 4.63; N, 12.25. Found: C, 55.14; H, 4.80; N, 12.15.

EXAMPLE 32

Preparation of the 4,5,6,7-Tetrahydro-1H-1,3-diazepin-2-ylhydrazone of 4,4′-bis(Trifluoromethyl)chalcone hydrochloride A mixture of 6.1 gm. (0.0178 mole) of 4,4′-bis(trifluoromethyl)chalcone, 2.93 gm. (0.0178 mole) of 2-hydrazino-4,5,6,7-tetrahydro-1H-1,3-diazepine hydrochloride and 3 drops of concentrated hydrochloric acid in 75 ml. of n-propanol is boiled for 2 hours and cooled overnight. The product is collected yielding 2.5 gm., melting point 230°–233°C.

Analysis calculated for $C_{22}H_{21}N_4ClF_6 \cdot HCl$: C, 53.84; H, 4.31; N, 11.42. Found: C, 53.75; H, 4.07; N, 11.27.

EXAMPLE 33

Preparation of the 4,5,6,7-Tetrahydro-1H-1,3-diazepin-2-ylhydrazone of 4-Bromo-4′-chlorochalcone hydrochloride A mixture of 3.2 gm. (0.01 mole) of 4-bromo-4′-chlorochalcone, 1.7 gm. (0.01 mole) of 2-hydrazino-4,5,6,7-tetrahydro-1H-1,3-diazepine hydrochloride and 1 ml. of concentrated hydrochloric acid in 100 ml. of 80% ethanol is stirred at reflux for 7 hours and then stirred at room temperature overnight. The precipitate is collected, washed with ether and dried at 60°C. under reduced pressure. The product is dissolved in 50 ml. of benzene and 50 ml. of chloroform at the boil, clarified and then cooled at −10°C. This mixture is diluted with 100 ml. of ether and allowed to stand at −10°C. The precipitate is collected, washed with ether and dried at 60°C. under reduced pressure.

Yield 0.6 gm., melting point 221°–224°C. Analysis calculated for $C_{20}H_{20}N_4ClBr \cdot HCl$: C, 51.30; H, 4.52; N, 11.97, Cl, 15.14; Br. 17.07. Found: C, 51.61; H, 4.49; N, 11.21, Cl, 15.99; Br, 15.99.

EXAMPLE 34

Preparation of the 4-Methyl-2-imidazolin-2-ylhydrazone of 4,4′-Dichlorochalcone hydrochloride A mixture of 3.10 gm. (0.0112 mole) of 4,4′-dichlorochalcone, 2.25 gm. (0.0112 mole) of 2-hydrazino-4-methyl-2-imidazoline dihydrochloride and 2 drops of concentrated hydrochloric acid in 100 ml. of ethanol is boiled for 1 hour. The mixture is concentrated to 15 ml. The mixture is concentrated twice with the addition of benzene to remove all ethanol. A 10 ml. portion of ether is added. Crystals form after about 1 hour. A 15 ml. portion of benzene is added and the product is collected by filtration, washed with benzene and dried yielding 3.39 gm., melting point 199°–200°C.

Analysis calculated for $C_{19}H_{18}N_4Cl_2 \cdot HCl$: C, 55.70; H, 4.67; N, 13.68. Found: C, 55.42; H, 4.80; N, 13.57.

EXAMPLE 35

Preparation of 4-Methyl-2-imidazolin-2-ylhydrazone of 4,4'-Dichloro-β-methylchalcone hydrochloride A mixture of 3.05 gm. (0.0105 mole) of 4,4'-dichloro-β-methylchalcone, 2.1 gm. (0.0112 mole) of 2-hydrazino-4-methyl-2-imidazoline dihydrochloride and 2 drops of concentrated hydrochloric acid in a mixture of 15 ml. of chloroform and 40 ml. of n-propanol is boiled for 1 hour and then concentrated to a gum which crystallizes from benzene-chloroform-hexane as white crystals. These crystals are washed with ethanol. Yield 2.47 gm., melting point 238°–240°C. Analysis calculated for $C_{20}H_{20}N_4Cl_2 \cdot HCl$: C, 56.69; H, 4.99; N, 13.22; Cl, 25.10. Found: C, 56.32; H, 4.94; N, 13.26; Cl, 24.97.

EXAMPLE 36

Preparation of the 4,5,6,7-Tetrahydro-1H-1,3-diazepin-2-ylhydrazone of 3,3-bis(p-Chlorophenyl)acrylophenone hydrochloride A mixture of 3.53 gm. (0.01 mole) of 3,3-bis(p-chlorophenyl)acrylophenone, 1.75 gm. (0.01 + mole) of 1-hydrazino-4,5,6,7-tetrahydro-1H-1,3-diazepine hydrochloride and 3 drops of concentrated hydrochloric acid in 50 ml. of n-propanol is boiled for 1 hour with the addition of about 0.1 gm. more of the hydrazine. The mixture is concentrated to a gum which is dissolved in chloroform. This mixture is concentrated and benzene and hexane are added. The product is collected and recrystallized from chloroform-benzene-hexane yielding 5.56 gm.

This product is recrystallized from chloroform-benzene-ether, followed by recrystallization from about 10 ml. of ethanol with chilling to −5°C., and finally from chloroform-benzene-ether yielding the title product as white crystals, 3.74 gm., melting point 154°–156°C.

Analysis calculated for $C_{26}H_{24}N_4Cl_2 \cdot HCL$: C, 62.48; H, 5.04; N, 11.21; Cl, 21.27. Found: C, 62.29; H, 5.07; N, 10.72; Cl, 20.79.

The starting material, 3,3-bis(4-chlorophenyl)acrylophenone is prepared by the procedure of Meyer and Schuster, Ber. 55, 819 (1923).

EXAMPLE 37

Preparation of the 4,5,6,7-Tetrahydro-1H-1,3-diazepin-2-ylhydrazone of 4,4'-bis(Methylthio)chalcone hydrochloride A slurry composed of 6.0 gm. (0.02 mole) of 4,4'-bis-(methylthio)chalcone, 3.4 gm. (0.02 + mole) of 2-hydra-4,5,6,7-tetrahydro-1H-1,3-diazepine hydrochloride and 10 drops of concentrated hydrochloric acid in 100 ml. of n-propanol is stirred at reflux for 3 hours, clarified while hot and then cooled at −10°C. A small portion of this is diluted with ether which induces a precipitate. This portion is then added to the main cold solution and maintained at −10°C. The precipitate is collected, washed with 100 ml. of cold n-propanol and then 100 ml. of ether and dried at 60°C. under reduced pressure.

Yield 4.9 gm., melting point 198°–200°C. Analysis calculated for $C_{22}H_{26}N_4S_2 \cdot HCl$: C, 59.10; H, 6.09; N, 12.53; S, 14.34; Cl, 7.93. Found: C, 58.84; H, 6.03; N, 12.49; S, 14.00; Cl, 7.91.

The starting material, 4,4'-bis(methylthio(chalcone, is prepared by the reaction of 4-methylthiobenzaldehyde and 4'-methylthioacetophenone in methanol solution in the presence of aqueous sodium hydroxide. After recrystallization from 2-methoxyethanol, the compound melts at 128°–129°C.

Analysis calculated for $C_{17}H_{16}OS_2$: C, 67.96; H, 5.37; S, 21.35. Found: C, 68.77; H, 5.50; S, 21.88.

EXAMPLE 38

Preparation of the 4,5,6,7-Tetrahydro-1H-1,3-diazepin-2-ylhydrazone of β, 4,4'-Trimethylchalcone hydrochloride A mixture of 4.2 gm. (0.0168 mole) of β, 4,4'-trimethylchalcone, 2.9 gm. (0.0176 mole) of 2-hydrazino-4,5,6,7-tetrahydro-1H-1,3-diazepine hydrochloride and 4 drops of concentrated hydrochloric acid in 50 ml. of ethanol is boiled for 1½ hours and then concentrated to a yellow gum, adding benzene to replace the ethanol. Ether is added and the mixture is triturated yielding a while solid. The solid is dissolved in chloroform and then filtered. The filtrate is concentrated adding benzene. The white crystals are collected and washed with benzene and ether and dried.

Yield 4.91 gm., melting point 138°–143°C. Analysis calculated for $C_{23}H_{28}N_4 \cdot HCl$: C, 69.60; H, 7.36; N, 14.11; Cl, 8.93. Found: C, 69.29; H, 7.37; N, 13.98; Cl, 8.83.

The starting material, β, 4,4'-trimethylchalcone is prepared by heating 4'-methylacetophenone and boric acid in xylene, the water being formed being removed in a water-separation apparatus. When water formation ceases, the reaction mixture is clarified, the xylene is removed, and the residual oil is distilled at 170°–180°C. The distillate solidifies on cooling, giving a pale yellow solid that melts at 55°–56°C.

EXAMPLE 39

Preparation of the 4,5,6,7-Tetrahydro-1H-1,3-diazepin-2-ylhydrazone of 1,1,3-tris(4-Chlorophenyl)-1-propen-3-one hydrochloride A mixture of 3.9 gm. (0.01 mole) of 4'-chloro-3,3-bis(p-chlorophenyl)acrylophenone, 1.9 gm. (0.01 + mole) of 2-hydrazino-4,5,6,7-tetrahydro-1H-1,3-diazepine hydrochloride and 2 drops of concentrated hydrochloric acid in 40 ml. of n-propanol is boiled for 1.5 hours with the addition of 0.15 gm. of hydrazine. The mixture is concentrated nearly to a gum, ether is added and the mixture is triturated to a gummy solid. This gum is dissolved in chloroform and then concentrated. The addition of ethanolic hydrochloric acid and benzene causes formation of a white solid. The solid is washed with ether and hexane and then recrystallized from ethanol and washed with ether yielding 1.71 gm., melting point 224°–225°C.

Analysis calculated for $C_{26}H_{23}N_4Cl_3 \cdot HCl$: C, 58.45; H, 4.53; N, 10.48; Cl, 26.54. Found: C, 58.25; H, 4.42; N, 10.61; Cl, 26.49.

The starting material, 1,1,3-tris(4-chlorophenyl)-1-propen-3-one is prepared by the procedure of W. T. Colwell, et al., J. Med. Chem., 14, 70 (1971).

EXAMPLE 40

Preparation of the 4,5,6,7-Tetrahydro-1H-1,3-diazepin-2-yl-hydrazone of 4-Chloro-4'-(methylsulfonyl)-chalcone hydrochloride A mixture of 6.4 gm. (0.02 mole) of 4-chloro-4'-(methylsulfonyl)chalcone, 3.5 gm. (0.02 + mole) of 2-hydrazino-4,5,6-7-tetrahydro-1H-1,3-diazepine hydrochloride and 10 drops of concentrated hydrochloric acid in 100 ml. of n-propanol is stirred at reflux for 4½ hours, clarified and cooled at −10°C. The precipitate is collected, washed with cold n-propanol and then ether and dried at 60°C. under reduced pressure. Yield 5.1 gm., melting point 232°–234°C.

Analysis calculated for $C_{21}H_{23}N_4O_2SCL$ . HCl: C, 53.96; H, 5.18; N, 11.99; S, 6.86; Cl, 15.17. Found: C, 53.27; H, 5.17; N, 11.55; S, 6.84; Cl, 14.87.

The starting material, 4-chloro-4'-methylsulfonylchalcone, is prepared by the reaction of 4-chloro-4-methylthiochalcone and 30% hydrogen peroxide in acetic acid solution. Dilution with water gives the crude product which after recrystallization from hot acetic acid, melts at 190°–191°C.

EXAMPLE 41

Preparation of the 4,5,6,7-Tetrahydro-1H-1,3-diazepin-2-ylhydrazone of 4'-Chloro-4-(methylthio)chalcone hydrochloride A mixture of 5.8 gm. (0.02 mole) of 4'-chloro-4-(methylthio)chalcone, 3.5 gm. (0.02 + mole) of 2-hydrazino14,5,6,7,-tetrahydro-1H-1,3-diazepine hydrochloride and 10 drops of concentrated hydrochloric acid in 100 ml. of n-propanol is stirred at reflux for 4½ hours, clarified and cooled at −10°C. The precipitate is collected, washed with 50 ml. of cold n-propanol and then 100 ml. of ether and air dried. This solid is dissolved in 100 ml. of chloroform and 200 ml. of benzene at the boil, carified and cooled at −10°C. The mixture is concentrated to about 75 ml., diluted with 125 ml. of benzene and heated to boiling. This mixture is diluted to 500 ml. with ether and cooled at −10°C. The precipitate is collected, washed with 400 ml. of ether and dried at 60°C. under reduced pressure. Yield 4.1 gm., melting point 218°–220°C.

Analysis calculated for $C_{21}H_{23}N_4SCl$ . HCl: C, 57.93; H, 5.56; N, 12.87; S, 7.36; Cl, 16.29. Found: C, 57.77; H, 5.57; N, 13.22; S, 8.07; Cl, 16.40.

The starting material, 4'-chloro-4-methylthiochalcone, is prepared by the reaction of 4-methylthio benzaldehyde and 4'-chloroacetophenone in ethanol solution in the presence of aqueous sodium hydroxide. After recrystallization from an ethanol-di-methylformamide mixture, the compound melts at 146°–147°C.

EXAMPLE 42

Preparation of the 4,5,6,7-Tetrahydro-1H-, 1,3-diazepin-2-ylhydrazone of 4-Chloro-4+-(methylthio)chalcone hydrochloride A mixture of 5.7 gm. (0.02 mole) of 4-chloro-4'-(methylthio)chalcone, 3.5 g,. (0.02 + mole) of 2-hydrazine-4,5,6,7-tetrahydro-1H-,1,3-diazepine hydrochloride and 10 drops of concentrated hydrochloric acid in 100 ml. of n-propanol is stirred at reflux for 5 hours, clarified while hot and then cooled at −10°C. The precipitate is collected, washed with cold n-propanol and then ether and dried at 60°C. under reduced pressure. Yield 0.9 gm., melting point 209°–212°C.

Analysis calculated for $C_{21}H_{23}N_4SCl$ . HCl: C, 57.93; H, 5.56; N, 12.87; S, 7.36; cl, 16.29. Found: c, 57.91; H, 5.59; N, 12.59; S, 7.37;Cl, 15.91.

The starting material, 4-chloro-4'-methylthiochalcone, is prepared by the reaction of 4-chlorobenzaldehyde and 4'-methylthioacetophenone in ethanol solution in the presence of aqueous sodium hydroxide. After recrystallization from 2-methoxyethanol, the compound melts at 159°–160°C.

EXAMPLE 43

Preparation of the 2-Imidazolin-2-ylhydrazone of 4'-Chloro-4-methoxychalcone hydrochloride A mixture of 4.8 g,. of 4'-chloro-4-methoxychalcone, 2.4 gm. of 2-hydrazino-2-imidazoline hydrochloride and 10 drops of concentrated hydrochloric acid in 100 ml. of n-propanol is stirred at reflux for 7 hours, clarified and cooled at −10°C. The solution is diluted with 100 ml. of ether and cooled at −10°C. The mixture is filtered and the filtrate is cooled at −10°C. The precipitate is collected, washed with ether and dried at 60°C. under reduced pressure. Yield 3.8 gm., melting point 206°–207°C.

Analysis calculated for $C_{19}H_{19}N_4OCl$ . HCl: C, 58.32; H, 5.15; N, 14.32; Cl, 18.12. Found: C, 58.05; H, 5.35; N, 14.15; Cl, 17.96.

The starting material, 4'-chloro-4-methoxyacetophenone, is prepared by the procedure of F. Straus and H. Blankenhorn, Ann., 415, 232 (1918).

EXAMPLE 44

Preparation of the 1,4,5,6-Tetrahydro-2-pyrimidinylhydrazone of 4'-Chloro-2,4,5-triethoxychalcone hydrochloride A mixture of 5.6 gm. (0.015 mole) of 4'-chloro-2,4,5-triethoxychalcone, 2.4 gm. (0.015 + mole) of 2-hydrazino-2-imidazoline hydrochloride and 10 drops of concentrated hydrochloric acid in 100 ml. of n-propanol is stirred at reflux for 1 hour and then at room temperature overnight. This mixture is refluxed for 3 more hours, clarified while hot and then cooled at −10°C. The precipitate is collected, washed with 50 ml. of cold n-propanol and then 100 ml. of ether and dried at 60°C. under reduced pressure. Yield 6.6 gm., melting point 237°–238°C.

Analysis calculated for $C_{25}H_{31}N_4O_3Cl$ . HCl: C, 59.17; H, 6.36; N, 11.04; Cl, 13.97. Found: C, 58.94; H, 6.44; N, 10.99; Cl, 13.87.

The starting material, 4'-chloro-2,4,5-triethoxychalcone, is prepared by the reaction of 4'-chloroacetophenone and 2,4,5-triethoxybenzaldehyde in ethanol solution in the presence of aqueous sodium hydroxide. After recrystallization from isopropanol, the compound melts at 128°–130°C.

EXAMPLE 45

Preparation of the 1,4,5,6-Tetrahydro-2-pyrimidinylhydrazone of 4'-Chloro-3,4,5-trimethoxychalcone hydrochloride A mixture of 5.0 gm. (0.015 mole) of 4'-chloro-3,4,5-trimethoxychalcone, 2.4 gm. (0.015 + mole) of 2-hydrazino-1,4,-5,6-tetrahydro-pyrimidine hydrochloride and 10 drops of concentrated hydrochloric acid in 100 ml. of n-propanol is stirred at reflux for 5 hours, clarified while hot and cooled at −10°C. The precipitate is collected, washed with 100 ml. of cold n-propanol and 100 ml, of ether and dried at 60°C. under reduced pressure. Yield 3.2 gm., melting point 231°–232°C.

Analysis calculated for $C_{22}H_{25}N_4O_3Cl \cdot HCl$: C, 56.78; H, 5.63; N, 12.04; Cl, 15.24. Found: C, 56.77; H, 5.74; N. 11.91; C;, 14.88.

The starting material, 4′-chloro-3,4,5-trimethoxychalcone, is prepared by the reaction of 4′-chloroacetophenone and 3,4,5-trimethoxybenzaldehyde in ethanol containing aqueous sodium hydroxide. After recrystallization from ethanol, the compound melts at 123°–124°C.

EXAMPLE 46

Preparation of the 4,5,6,7-Tetrahydro-1H-,1,3-diazepin-2-ylhydrazone of 4-Chloro-3′,4′-dimethylchalcone hydrochloride A mixture of 2.80 gm. (0.01 + mole) of 4-chloro-3′,-4′-dimethylchalcone, 1.80 gm. (0.01 + mole) of 2-hydrazino-4,5,6,7-tetrahydro-1H-,1,3-diazepine hydrochloride and 6 drops of concentrated hydrochloric acid in 60 ml. of n-propanol is boiled for 30 minutes and concentrated. The mash is filtered and washed with ethanol-ether obtaining a white solid. This solid is recrystallized by dissolving in chloroform, concentrating and adding ethanol. Yield 1.22 gm., melting point 239°–240°C. Analysis calculated for $C_{22}H_{25}N_4Cl \cdot HCl \cdot \frac{1}{4} H_2O$: C, 62.65; H, 6.32; N, 13.29 ; Cl, 16.80. Found: C, 62.46; H, 6.32; N, 13.47; Cl, 16.71.

The starting material, 4-Chloro-3′,4′-dimethylchalcone is prepared by the reaction of 4-chlorobenzaldehyde and 3′,4′-dimethylacetophenone in ethanol solution containing aqueous sodium hydroxide. After recrystallization from benzene, the compound melts at 156°–157°C.

EXAMPLE 47

Preparation of the 4,5,6,7-Tetrahydro-1H-1,3-diazepin-2-ylhydrazone of β, 2,2′,5,5′-Pentamethylchalcone A mixture of 5.7 gm. (0.02 mole) of β, 2,2′,5,5′-pentamethylchalcone, 3.3 gm. (0.02 mole) of 2-hydrazino-4,5,6,7-tetrahydro-1H-, 1,3-diazepine hydrochloride and 3 drops of concentrated hydrochloric acid in 60 ml. of n-propanol is boiled for 1 hour, cooled and concentrated. The yellow gum is treated with excess sodium hydroxide solution, extracted with 100 ml. of chloroform, and the chloroform removed under reduced pressure, leaving a glass which is powdered to a yellow solid.

Yield 5.28 gm., melting point 57°–68°C. Analysis calculated for $C_{25}H_{32}N_4$: C, 77.28; H, 8.30; N, 14.42. Found: C, 76.50; H, 8.36; N, 14.43.

The starting material, β, 2,2′5,5′-pentamethylchalcone, is prepared by heating 2,5-dimethylacetophenone and boric acid in xylene, the water formed being collected in a water separation device. When water formation ceases, the mixture is clarified and the desired compound separated by fractional distillation of the filtrate. It is a viscous oil that resists attempts at crystallization.

EXAMPLE 48

Preparation of 1,4,5,6-Tetrahydropyrimidine-2-hydrazone of 4-chloro-4′-methylthiochalcone hydrochloride A mixture consisting of 5.8 gm. of 4-chloro-4′-methylthiochalcone, 3.3 gm. of 2-hydrazino-1,4,5,6-tetrahydropyrimidine hydrochloride, 100 ml. of n-propanol, and 10 drops of concentrated hydrochloric acid is stirred at reflux for 4 hours. The hot solution is clarified and cooled at −10°C. There is obtained 4.5 gm. of the title compound, melting at 218°–220°C. with decomposition.

Analysis calculated for $C_{20}H_{21}N_4SCl \cdot HCl$; C, 57.00; H, 5.26; N, 13.30; S, 7.61; Cl, 16.83. Found: C, 56.67; H, 5.29; N, 12.97; S, 7.65; Cl, 16.60.

EXAMPLE 49

Preparation of the 1,4,5,6-Tetrahydropyrimidine-2-hydrazone of 4-Chloro-4′-dimethylthiocarbamoyloxychalcone hydrochloride n-propanalate A mixture consisting of 6.9 gm. of 4-chloro-4′-dimethylthiocarbamoylchalcone, 3.3 gm. of 2-hydrazino-1,4,5,6-tetrahydropyrimidine hydrochloride, 100 ml. of n-propanol, and 10 drops of concentrated hydrochloric acid is stirred at reflux for 90 minutes. The hot solution is clarified and cooled at −10°C. The product crystallizes with n-propanol of crystallization: yield 4.8 gm. It softens at 120°c. and melts clearly at 145°C.

Analysis calculated for $C_{22}H_{24}N_5OSCl \cdot HCl \cdot C_3H_7OH$: C, 55.75; H, 6.18, N, 13.01; S, 5.95; Cl, 13.17. Found: C, 55.33; H, 5.43; N, 12.89; S, 5.87; Cl, 12.84.

The starting material, 4-chloro-4′-dimethylthiocarbamoyloxychalcone is prepared by the reaction of 4-chloro-4′-hydroxy chalcone and dimethylthiocarbamyl chloride in acetone solution in the presence of aqueous sodium hydroxide. After recrystallization from acetone, it melts at 177°–178°C.

Analysis calculated for $C_{18}H_{16}NSO_2Cl$: C, 62.51; H, 4.66; N, 4.05; S, 9.27; Cl, 10.25. Found: C, 62.69; H, 4.65; N, 3.94; S, 9.33; Cl, 10.21.

EXAMPLE 50

Preparation of the 5,5-Dimethyl-1,4,5,6-tetrahydropyrimidine-2-hydrazone of 4-Chloro-4′-methylthiochalcone hydrobromide A mixture consisting of 4.3 gm. of 4-chloro-4′-methylthiochalcone, 3.5 gm. of 5,5-dimethyl-2-hydrazino-1,4,5,6-tetrahydropyrimidine hydrobromide, 100 ml. of n-propanol and 5 drops of 48% hydrobromic acid is stirred under reflux for 90 minutes. The solution is clarified and cooled at room temperature. The initial precipitate is removed by filtration, and the filtrate is cooled at −10°C. The title compound is obtained pure and melts at 205°–206°C.

Analysis calculated for $C_{22}H_{25}N_4SCl \cdot HBr$: C, 53.50; H, 5.31; N, 11.34; S, 6.49. Found: C, 53.55; H, 5.73; N, 10.93; S, 6.45.

EXAMPLE 51

Preparation of the 2-Imidazolinyl-2-hydrazone of 3-(2Naphthyl)-2′-acrylonaphtone hydrobromide A mixture of 6.1 gm. of 3-(2-naphthyl)-2′-acrylonaphthone, 4gm. of 2hydrazino-2-imidazoline hydrobromide, 100 ml. of n-propanol, and 5 drops of 48% hydrobromic acid is refluxed for 6 hours. Cooling the solution at −10°C. gives 5.8 gm. of pure compound melting at 215°–217°C.

Analysis calculated for $C_{26}H_{22}N_4$. HBr: C, 66.25; H, 4.92; N, 11.89; Br, 16.95. Found; C, 65.94; H, 4.91; N, 11.63; Br, 16.43.

The starting material, 3-(2-naphthyl)-2'-acrylonaphthone is prepared by the reaction of 2-naphthaldehyde and 2-acetonaphthone in ethanol containing aqueous sodium hydroxide. After recrystallization from 2-methoxyethanol, it melts at 201°–202°C.

EXAMPLE 52

Preparation of the 1,4,5,6-Tetrahydropyrimidine-2-hydrazone of 4'-Chloro-3,5-dimethylchalcone hydrochloride A mixture of 2.8 gm. of 4'-chloro-3,5-dimethylchalcone, 1.7 gm. of 2-hydrazino-1,4,5,6-tetrahydropyrimidine hydrochloride, 40 ml. of n-propanol and 2 drops of concentrated hydrochloric acid are refluxed for 1 hour. The solution is then concentrated to 15 ml. of volume and 20 ml. of diethyl ether added. The white precipitate is collected and recrystallized from a mixture of chloroform and benzene, giving 2.6 gm. of the pure compound, melting at 237°238°C.

Analysis calculated for $C_{21}H_{23}N_4Cl$ . HCl: C, 62.54; H, 6.00; N, 13.89; Cl, 17.57. Found: C, 62.56; H, 6.20; N, 14.04; Cl, 17.69.

The starting material, 4'-chloro-3,5-dimethylchalcone is prepared by the reaction of 3,5-dimethylbenzaldehyde and 4'-chloroacetophenone in ethanolic solution in the presence of aqueous sodium hydroxide. It melts at 62°–62.5°C.

EXAMPLE 53

Preparation of the 1,4,5,6-Tetrahydropyrimidine-2-hydrazone of 4,4'-Bis(methylthio)-β-methylchalcone hydrochloride A mixture consisting of 3.14 gm. of 4,4'-bis(methylthio)-62 -methylchalcone, 1.6 gm. of 2-hydrazino-1,4,5,6-tetrahydropyrimidine hydrochloride, 75 ml. of n-propanol and 2 drops of concentrated hydrochloric acid is refluxed for 90 minutes and clarified hot. Cooling the filtrate yielded a white precipitate which after recrystallization from ethanol gave 1.9 gm. of pure product, melting at 253°–254°C.

Analysis calculated for $C_{22}H_{26}N_4S_2$. HCl: C, 59.11; H, 6.09; N, 12.53; S, 14.34; Cl, 7.93. Found: C, 59.20; H, 6.21; N, 12.62; S, 14.50; Cl, 7.93.

The starting material, 4,4'-bis(methylthio)-β-methyl chalcone is prepared by the self condensation of 4'-methylthioacetophenone in boiling toluene solution in the presence of aluminum t-butoxide. After recrystallization from acetone, it melted at 121°–122°C.

EXAMPLE 54

Preparation of the 1,4,5,6-Tetrahydropyrimidine-2-hydrazone of 4'-Methylthio-4-phenylchalcone hydrochloride A mixture of 6.6 gm. of 4'-methylthio-4-phenylchalcone, 3.5 gm. of 2-hydrazino-1,4,5,6-tetrahydropyrimidine hydrochloride, 100 ml. of n-propanol, and 10 drops of concentrated hydrochloric acid are heated under reflux for 4 hours. The hot solution is clarified and cooled at −10°C. An orange-yellow precipitate is formed. It is collected, washed with n-propanol and diethyl ether, and dried; yield, 6.9 gm., melting point 235°–236°C.

Analysis calculated for $C_{26}H_{26}N_4S$ . HCl: C, 67.44; H, 5.88; N, 12.10; S, 6.92; Cl, 7.66. Found: C, 66.84; H, 6.11; N, 12.23; S, 6.63; Cl, 7.75.

The starting material, 4'-methylthio-4-phenylchalcone is prepared by the reaction of 4-biphenylcarboxaldehyde and 4'-methylthioacetophenone in ethanol solution in the presence of aqueous sodium hydroxide. Recrystallization from 2-methoxyethanol gave the pure compound, melting at 142°–143°C.

EXAMPLE 55

Preparation of the 1,4,5,6-Tetrahydropyrimidine-2-hydrazone of 4-Bromo-4'-methylthiochalcone hydrochloride A mixture consisting of 6.7 gm. of 4-bromo-4'-methyl-thiochalcone, 3.4 gm. of 2-hydrazino-1,4,5,6-tetrahydropyrimidine hydrochloride, 100 ml. of n-propanol, and 10 drops of concentrated hydrochloric acid is stirred under reflux for 4 hours. Clarification of the hot solution and cooling at −10°C. gave 4.2 gm. of the pure title compound melting at 225°–226°C.

Analysis calculated for $C_{20}H_{21}N_4BrS$ . HCl: C, 51.56; H, 4.76; N, 12.03, S. 6.88; Cl, 7.61; Br, 17.15. Found: C, 51.02; H, 4.81; n, 11.58; S, 6.94; Cl, 7.69; Br, 17.34.

The starting material, 4-bromo-4'-methylthiochalcone is prepared by the reaction of 4-biphenylcarboxaldehyde and 4'-bromoacetophenone in ethanol solution in the presence of aqueous sodium hydroxide. Recrystallization from 2-methoxyethanol gave the pure compound melting at 174°–175°C.

Analysis calculated for $C_{16}H_{13}SOBr$: C, 57.67; H, 3.93; S, 9.62; Br, 23.98. Found: C, 58.07; H, 3.88; S, 9.91; Br, 23.91.

EXAMPLE 56

Preparation of the 2-Imidazolinyl-2-hydrazone of 4'-Methylthio-3-(2-naphthyl)acrylophenone hydrochloride A mixture of 6.1 gm. of 4'-methylthio-3-(2-naphthyl)-acrylophenone, 4.0 gm. of 2-hydrazino-2-imidazoline hydrobromide, 100 ml. of n-propanol and 10 drops of 48% hydrobromic acid are heated under reflux. Within 10 minutes, a heavy precipitate is present, necessitating addition of 75 ml of n-propanol to permit stirring. After 4 hours of heating, the mixture is filtered hot, the precipitate washed with n-propanol and diethylether, and dried; yield, 7.7 gm., melting point 232°–233°C.

Analysis calculated for $C_{23}H_{22}N_4S$ . HBr: C, 59.10; H, 4.96; N, 11.99; S, 6.86; Br, 17.09. Found: C, 59.16; H, 5.17; N, 12.00; S, 6.92; Br, 16.87.

The starting material, 4'-methylthio-3-(2-naphthyl)-acrylophenone, is prepared by the reaction of 2-naphthaldehyde and 4'-methylthioacetophenone in ethanol solution in the presence of aqueous sodium hydroxide. After recrystallization from a mixture of 2-methoxyethanol and dimethylformamide, it melts at 196°–197°C.

EXAMPLE 57

Preparation of the 1,4,5,6-Tetrahydropyrimidine-2-hydrazone of 1,1,3-Tris(4-chlorophenyl)-1-propen-3-one hydrochloride A mixture comprising 3.87 gm. of 1,1,3-tris(4-chlorophenyl)-1-propen-3-one, 1.65 gm. of 2-hydrazino-1,4,5,6-tetrahydropyrimidine hydrochloride, 40 ml. of n-propanol and 2 drops of concentrated hydrochloric acid is refluxed for 1 hour and then concentrated to dryness under reduced pressure. The resultant gum is dissolved in hot chloroform, the solution clarified, and the chloroform removed under reduced pressure. The residual solid is recrystallized from ethanol to give 3.6 gm. of pure compound melting at 252°–253°C.

Analysis calculated for $C_{25}H_{21}N_4Cl_3 \cdot HCl$: C, 57.72; H, 4.26; N, 10.76; Cl, 27.26. Found: C, 57.46; H, 4.35; N, 10.63; Cl, 27.16.

EXAMPLE 58

Preparation of the 2-imidazolinyl-2-hydrazone hydrobromide of 4-Chloro-4'-Iodochalcone A mixture comprising 7.4 g. of 4-chloro-4'-iodochalcone, 4.0 g. of 2-hydrazino-2-imidazoline hydrobromide, 10 drops of 48% hydrobromic acid and 125 ml. of n-propanol is stirred and heated under a reflux condenser for 3 hours. The hot solution is clarified and cooled at −10°C. The tan precipitate that forms is collected, washed with cold n-propanol and ether, and dried; yield, 5.1 g., melting point 207°–210°C.

Analysis calculated for: $C_{18}H_{16}N_4$ I Cl. HBr:; C, 40.67; H, 3.22; N, 10.54. Found: C, 41.11; H, 3.29; N, 10.52.

The starting material, 4-chloro-4'-iodochalcone is prepared by the reaction of 4-chlorobenzaldehyde and 4'-iodoacetophenone in ethanolic solution in the presence of aqueous sodium hydroxide. After recrystallization from 2-methoxyethanol, it melts at 189°–190°C.

We claim:
1. A substituted chalcone of the formula:

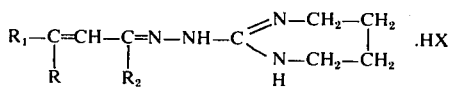

wherein $R_1$ and $R_2$ are the same or different and are selected from the group consisting of monohalophenyl, monomethylphenyl, dimethylphenyl, $C_1$-$C_4$-alkylthiophenyl, methylsulfonylphenyl, trifluoromethylphenyl and biphenylyl; R is hydrogen or methyl and X is chloro, iodo or bromo.

2. The substituted chalcone in accordance with claim 1,4,5,6,7-tetrahydro-1H-1,3-diazepin-2-ylhydrazone of 4,4'-dichloro-62-methylchalcone hydrochloride.

3. The substituted chalcone in accordance with claim 1,4,5,6,7-tetrahydro-1H-1,3-diazepin-2-ylhydrazone of 4,4'-dichlorochalcone hydrochloride.

4. The substituted chalcone in accordance with claim 1,4,5,6,7-tetrahydro-1H-, 1,3-diazepin-2-ylhydrazone of 4-chloro- 4'-(methylthio)chalcone hydrochloride.

5. The substituted chalcone in accordance with claim 1,4,5,6,7-tetrahydro-1H-1,3-diazepin-2-ylhydrazone of 4-bromo-4'-chlorochalcone hydrochloride.

6. The substituted chalcone in accordance with claim 1 4,5,6,7-tetrahydro-1H-1,3-diazepin-2-ylhydrazone of 4'-chloro-4-(trifluoromethyl)chalcone hydrochloride.

7. The substituted chalcone in accordance with claim 1, 4,5,6,7-tetrahydro-1H-1,3-diazepin-2-ylhydrazone of 4,4-bis(trifluoromethyl)chalcone hydrochloride.

8. The substituted chalcone in accordance with claim 1, 4,5,6,7-tetrahydro-1H-1,3-diazepin-2-ylhydrazone of 4,4'-bis(methylthio)chalcone hydrochloride.

9. The substituted chalcone in accordance with claim 1, 4,5,6,7-tetrahydro-1H-1,3diazepin-2-ylhydrazone of β, 4,4'-trimethylchalcone hydrochloride.

10. The substituted chalcone in accordance with claim 1, 4,5,6,7-tetrahydro-1H-1,3-diazepin-2-ylhydrazone of 4-chloro-4'-(methylsulfonyl)chalcone hydrochloride.

11. The substituted chalcone in accordance with claim 1, 4,5,6,7-tetrahydro-1H-1,3-diazepin-2-ylhydrazone of 4'-chloro-4-(methylthio)chalcone hydrochloride.

12. The substituted chalcone in accordance with claim 1, 4,5,6,7-tetrahydro-1H, 1,3-diazepin-2-ylhydrazone of 4-chloro-3',4'-dimethylchalcone hydrochloride.

13. The substituted chalcone in accordance with claim 1, 4,5,6,7-tetrahydro-1H-1,3-diazepin-2-ylhydrazone of β, 2,2',5,5'-pentamethylchalcone.

* * * * *

UNITED STATES PATENT OFFICE
CERTIFICATE OF CORRECTION

PATENT NO. : 3,931,152
DATED : January 6, 1976
INVENTOR(S) : Andrew Stephen Tomcufcik, Raymond George Wilkinson, Ralph Grassing Child It is certified that error appears in the above-identified patent and that said Letters Patent are hereby corrected as shown below:

Column 24, Claim 2 last line "62" should be -- $\beta$ --.

Column 24, Claim 4 second line "4,5,6,7-tetrahydro-1H-, 1,3-diazepine-2-ylhydrazone" should read -- 4,5,6,7-tetrahydro-1H-1,3-diazepine-2-ylhydrazone --.

Signed and Sealed this thirteenth Day of April 1976

[SEAL]

Attest:

RUTH C. MASON
Attesting Officer

C. MARSHALL DANN
Commissioner of Patents and Trademarks